United States Patent
Avevor et al.

(10) Patent No.: US 7,335,053 B2
(45) Date of Patent: Feb. 26, 2008

(54) ECG CABLE MANAGEMENT SYSTEM

(75) Inventors: Philip Avevor, Jacksonville, FL (US); Roger K. J. Salani, Pittsburgh, PA (US); Peter Schonning, Jacksonville, FL (US); Percy F. Shadwell, Jacksonville, FL (US)

(73) Assignee: I.Q. Innovations, LLC, Jacksonville, FL (US)

( * ) Notice: Subject to any disclaimer, the term of this patent is extended or adjusted under 35 U.S.C. 154(b) by 31 days.

(21) Appl. No.: 11/425,136

(22) Filed: Jun. 19, 2006

(65) Prior Publication Data
US 2006/0286861 A1 Dec. 21, 2006

Related U.S. Application Data

(60) Provisional application No. 60/595,238, filed on Jun. 17, 2005.

(51) Int. Cl.
*H01R 13/72* (2006.01)
(52) U.S. Cl. ...................................... 439/502
(58) Field of Classification Search .................. 174/50, 174/53; 439/501, 502
See application file for complete search history.

(56) References Cited

U.S. PATENT DOCUMENTS

| 6,077,108 A * | 6/2000 | Lorscheider et al. | 439/501 |
| 6,325,665 B1 * | 12/2001 | Chung | 439/501 |
| 6,780,047 B1 * | 8/2004 | Laity et al. | 439/501 |

* cited by examiner

*Primary Examiner*—Briggitte R. Hammond
(74) *Attorney, Agent, or Firm*—Mark Young, P.A.

(57) ABSTRACT

A scalable cable management system comprises an electronics module with a microcontroller; a plurality of drive modules and a releasably engaged cable cartridge for each drive module. Each cable cartridge houses a lead wire cable spool with an electrical slip ring connected to the wire. Stationary electrical contacts pickup signals from the slip ring for use by the electronics module. A device such as an electric or spring-driven motor, with a gear train and an optional clutch, controllably rotate the cable spool. A cleaning assembly cleans portions of the lead wire as it is extended or retracted. The microcontroller receives strain signals representative of tension on a lead wire from cable strain gauge. The electronics module may also include a defibrillator protection sub-system, a crossbar transfer switch, an instrumentation amplifier and a communications unit. Test terminals are also provided for assessing integrity of each lead wire.

20 Claims, 11 Drawing Sheets

ECG CABLE MANAGEMENT SYSTEM

RELATED APPLICATION

This application claims the benefit of priority of U.S. Provisional Application 60/595,238, filed Jun. 17, 2005, the entire contents of which are incorporated herein.

FIELD OF THE INVENTION

This invention relates to medical equipment such as electrocardiogram (ECG) equipment, and more particularly, to a system for managing extension and retraction of ECG leads, and interfacing electrocardiogram equipment with the leads.

BACKGROUND

Medical equipment such as electrocardiogram equipment utilize a plurality of sensors (e.g., electrodes) to measure physiological parameters. Cables or lead wires connect the sensors to the medical equipment. The sensors typically include adhesive pads. Typically several sensors are applied to a patient to obtain the necessary signals. The raw signals are fed to a processing device such as a computer or electrocardiogram device.

One serious problem with current equipment is tangling. ECG leads may be several feet long. Those skilled in the field will readily appreciate that the cables can easily become tangled with each other and with cables for other sensors, especially during extension and storage. Detangling consumes time, may delay an urgently needed medical procedure and causes premature failure of cables.

To help address the tangling problem, various retraction mechanisms have been conceived. However, such mechanisms generally rely exclusively on spring loaded retraction mechanisms without positive locking. These mechanisms have proven to be somewhat unreliable with a penchant for unintended retraction. This may result in a botched procedure, increased cost and delay of urgently needed medical treatment.

Another problem is that ECG leads may become contaminated during use due to contact with contaminants such as blood, other bodily fluids and medicinal preparations. Unfortunately, heretofore, contaminated ECG leads have been reused without adequate sterilization or decontamination.

Another problem is that the integrity of ECG leads often become compromised during repeated use. Bending, stressing and straining an ECG lead may cause structural failure, particularly in the case of radiolucent leads which are quite fragile. Structural defects may prevent transmission of signals or result in spurious signals.

Yet another problem is that various equipment may require signals from the same type of sensors. Rather than share a sensor, practitioners typically place separate sets of sensors (i.e., electrodes) on a patient. This results in additional clutter and a heightened risk of entanglement. Placement of numerous sensors also consumes additional time and may delay an urgently needed medical procedure.

What is lacking in the art is an effective device for managing ECG leads that utilizes a reliable retraction mechanism with positive locking, provides circuitry and interfaces for sharing signals, cleans cables during retraction and facilitates testing to ensure proper functionality. The subject invention is directed to overcoming one or more of the problems and fulfilling one or more of the needs as set forth above.

SUMMARY OF THE INVENTION

To overcome one or more of the problems and fulfill one or more of the needs as set forth above, in one aspect of an exemplary embodiment of the invention a cable management system is provided. The cable management system comprises an electronics module; a plurality of drive modules and a cable cartridge for each drive module. Each cable cartridge includes a housing defining an interior compartment and a cable opening configured to allow a cable to pass from the interior compartment through the cable opening. The cable cartridge further includes a cable spool rotatably mounted in the interior compartment of the housing and having an electrical slip ring. An electrically conductive lead wire has a first end and an opposite second end. The first end is mechanically attached to the spool and electrically connected to the slip ring. The lead wire is adapted for transmitting electrical signals. A stationary electrical contact maintains electrical communication with the slip ring. Each drive module includes means for electrically coupling the stationary electrical contact to the electronics module; means for releasably engaging a cable cartridge; and means for controllably rotating the cable spool. Means for communicating output signals from the electronics module to output signal cables is also provided. The means for communicating output signals from the electronics module to output signal cables may comprise a monitor output connector disposed between the output signal cables and the electronics module.

Each drive module may include an ejector configured to controllably release the corresponding cable cartridge from the drive module. Each drive module may also include at least one control device operably configured to control extension and retraction of the lead wire for the corresponding cable cartridge.

The output signal cables are adapted to communicate output signals to at least one ECG device, such as an ECG monitor, a heart synchronized pump, or a heart synchronized imaging device.

The cable cartridge may include a cleaning assembly adjacent to the cable opening and adapted to clean portions of the lead wire passing through the cable opening. The cleaning assembly may also include a squeegee assembly configured to slough off debris clinging to portions of the lead wire passing through the cable opening. The cleaning assembly may further include a disinfectant applicator configured to apply a disinfecting agent to portions of the lead wire passing through the cable opening. The cleaning assembly may also include a germicidal UV light source adapted to shine UVC light on portions of the lead wire passing through the cable opening.

The means for controllably rotating the cable spool may include a controllable drive motor and transmission adapted to transmit torque from the controllable drive motor to the cable spool. The drive motor may be communicatively coupled to the electronics module with the electronics module being configured to govern rotation and direction of the drive motor. Additionally, the transmission may include a torque slipping clutch mechanism adapted to transmit torque except when a determined torque is exceeded. Alternatively, the means for controllably rotating the cable spool may comprise a spring-driven rotation mechanism adapted to be charged as the lead wire is extended from the cable opening and adapted to relax as the lead wire is retracted through the cable opening.

The principles of the invention may be applied to any type of ECG lead wires, now known or hereafter developed. The lead wire may be radiopaque or radiolucent. By way of example and not limitation, each lead wire may be constructed of a shielded wire (e.g., coaxial) comprising an inner conductor surrounded by a mesh shield and an insulator outer layer. The inner conductor carries ECG signals and electrically connects an ECG sensor to the system's circuitry. The outer shield protects the ECG signals from radio frequency (RF) interference. Alternatively, for example, each ECG lead wire may comprise an unshielded, single-conductor wire with an insulated outer layer. The outer insulator layer may be comprised of a durable, flexible material that is impervious to bodily fluids, disinfectants and cleaning solvents, exhibits a high tensile strength, and can be sterilized using most common methods (e.g., steam autoclave, gamma irradiation, and ethylene oxide gas. Latex-free urethanes, Santoprene®, silicone or other compatible elastomers may be utilized.

The outer insulator layer may also be lubricated to facilitate retraction and extension. Lubrication may optionally be provided by any suitable lubricant, including fluorosilicone greases and oils. The insulator may be impregnated with a lubricant, externally lubricated or lubricated with a surface treatment. As one example, lubrication may be provided by coating the surface of the outer layer with one of the family of parylene compounds such as those available from Specialty Coating Systems, Inc., Indianapolis, Ind. Parylene compounds comprise a family of p-xylylene dimers that polymerize when deposited onto a surface to form a hydrophobic polymeric coating with a relatively low coefficient of friction. For example, an insulator according to principles of the invention may be coated with polymerized dichloro-(2, 2)-paracyclophane (Parylene C) or di-p-xylylene (Parylene N). The Parylene monomers may be applied to the surface of the outer layer by gas-phase deposition in a vacuum chamber.

The cable cartridge further include a cable strain gauge assembly configured to produce a strain signal representative of tension on the lead wire. The strain gauge assembly may include at least one resistive elastic sensor, the resistance of which is a function of applied strain. The strain gauge assembly is electrically coupled to the electronics module.

The electronics module may include a defibrillator protection sub-system configured to protect the electronics module discharges of a defibrillator. The electronics module may also include a crossbar transfer switch and an instrumentation amplifier having inverting and non-inverting inputs. The crossbar switch may be configured to selectively apply input signals received via the lead wire to one of inverting and non-inverting inputs of the instrumentation amplifier. The electronics module may also include a communications unit configured to communicate signals to and from the electronics module.

Each drive module may include a test terminal corresponding to each lead wire. Each lead wire may include a lead clip attached at the second end of the lead wire. The test terminal, which is adapted for engagement by the lead clip, is operably coupled to the electronics module. The electronics module includes a microcontroller configured to produce a test signal for the test terminal to test integrity of the lead wire.

BRIEF DESCRIPTION OF THE DRAWINGS

The foregoing and other aspects, objects, features and advantages of the invention will become better understood with reference to the following description, appended claims, and accompanying drawings, where:

Those skilled in the art will appreciate that the figures are not intended to be drawn to any particular scale. The invention is not limited to the exemplary embodiments depicted in the figures; the shapes, relative sizes or proportions shown in the figures; or the specific selection, arrangement or coordination of components shown in the figures.

DETAILED DESCRIPTION

With reference to the drawings, wherein like numerals represent like features, various sectional, perspective and exploded views of an exemplary ECG cable management system in accordance with principles of the invention is conceptually shown. For convenience of reference, the exemplary system is referred to herein as the device, system, ECG cable management system, ECG cable management system or the like.

Advantageously, the device includes mechanical retraction mechanisms to allow quick and easy storage and extension of ECG leads. Additionally, testing components are provided to test leads prior to every use. Furthermore, cleaning mechanisms enable automatic cleaning of leads as they are retracted. Moreover, the device is configured to allow a single set of ECG leads to supply signals to multiple monitoring devices.

Figure 1:
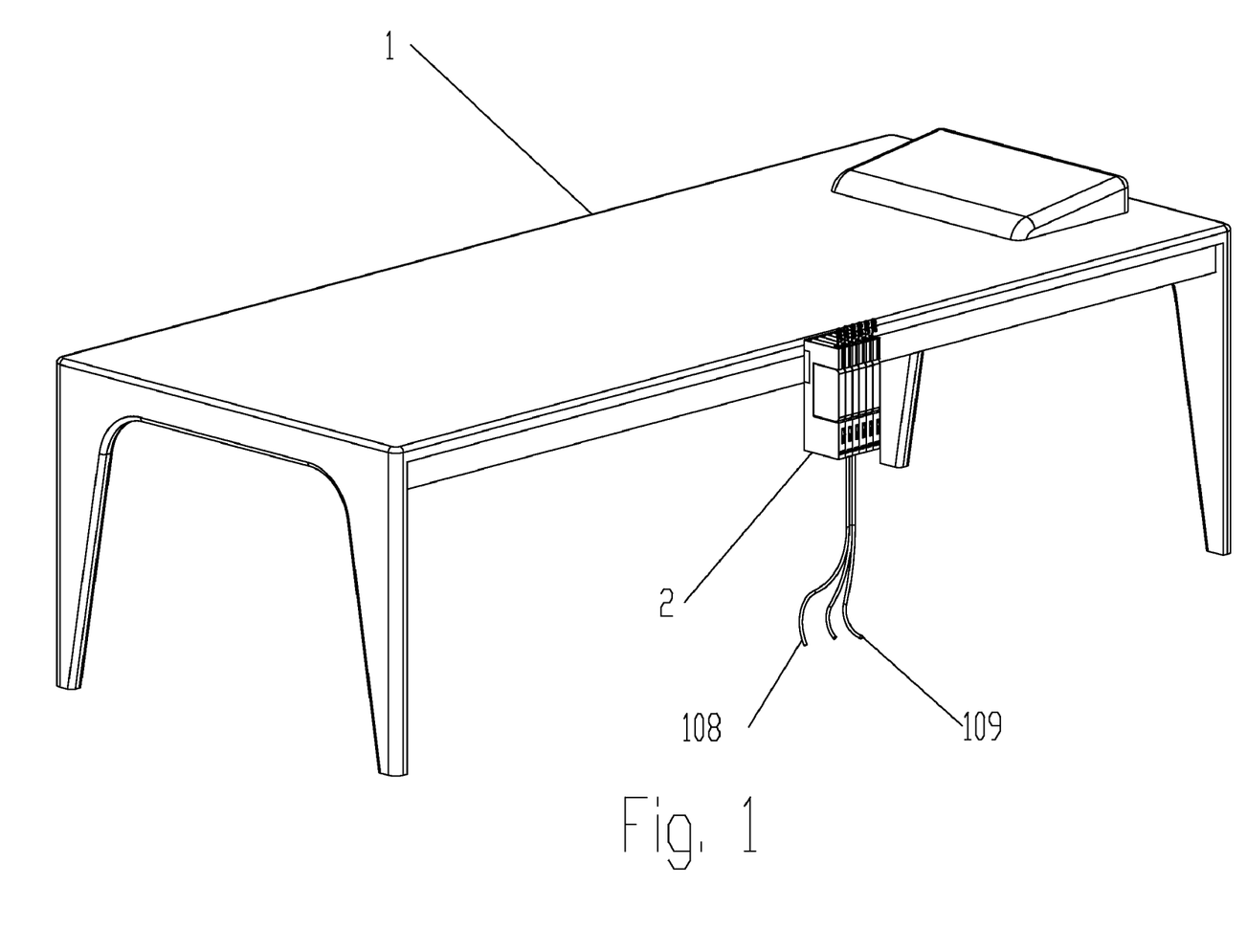
FIG. 1 provides a perspective view of an exemplary ECG cable management system attached to the side of a medical procedure table according to principles of the invention.

Referring to FIG. 1, a medical procedure bed or table such as an operating table 1 with an ECG cable management system 2 attached is shown. The exemplary system 2 is placed in proximity to the table 1 (or other support mechanism), and may be releasably or permanently attached to the table 1 (or other support mechanism). Any attachment mechanisms effective for releasably or permanently securing the system 2 to the table (or other support mechanism) may be utilized. Other support mechanisms may include a mobile ECG cart or any other kind of patient support mechanism. Wires 108, 109 exiting the system supply power to the system and communicate ECG signals to one or more monitoring devices.

Figure 2:
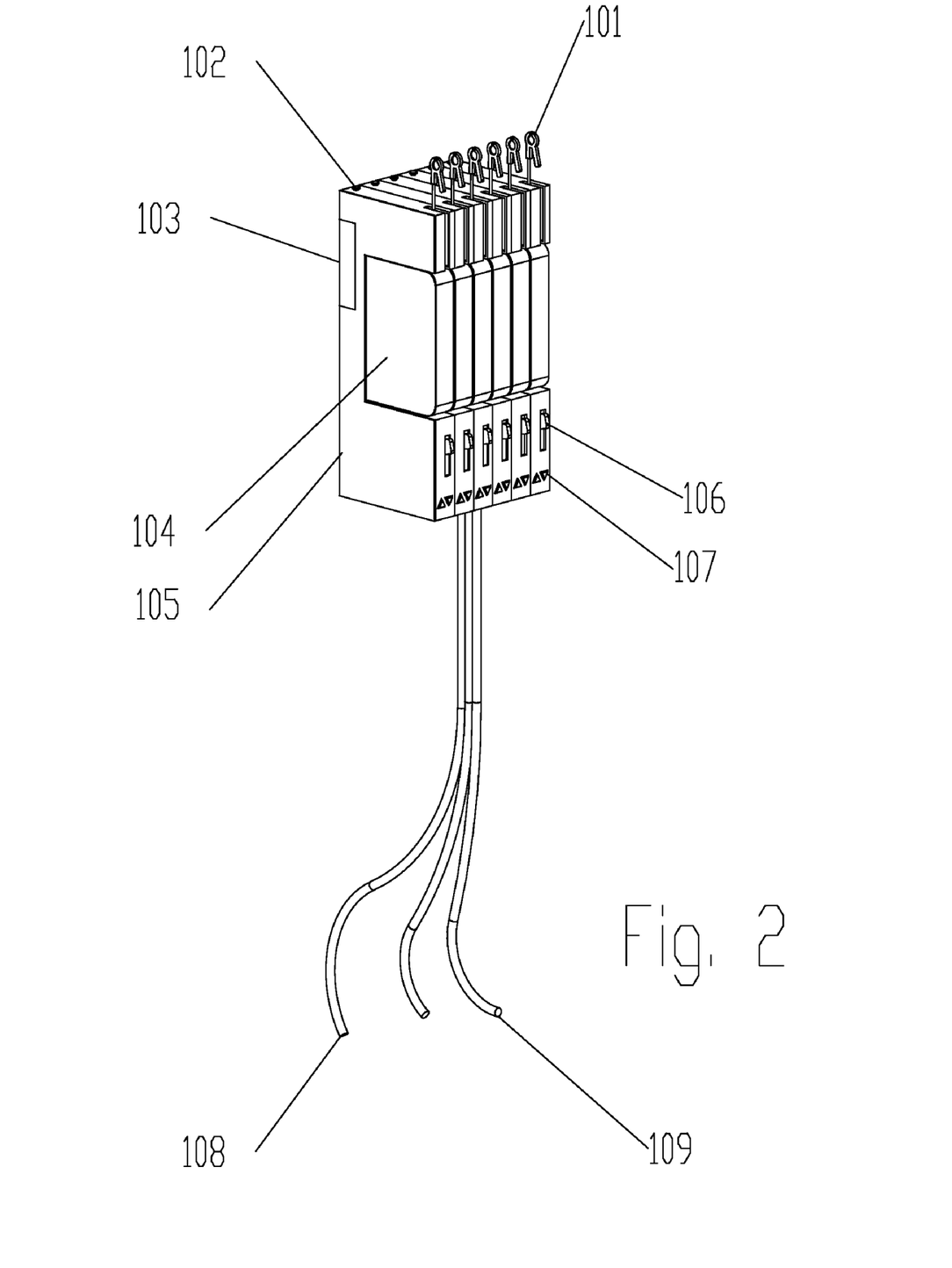
FIG. 2 provides a perspective view of an exemplary ECG cable management system according to principles of the invention.
Figure 4A:
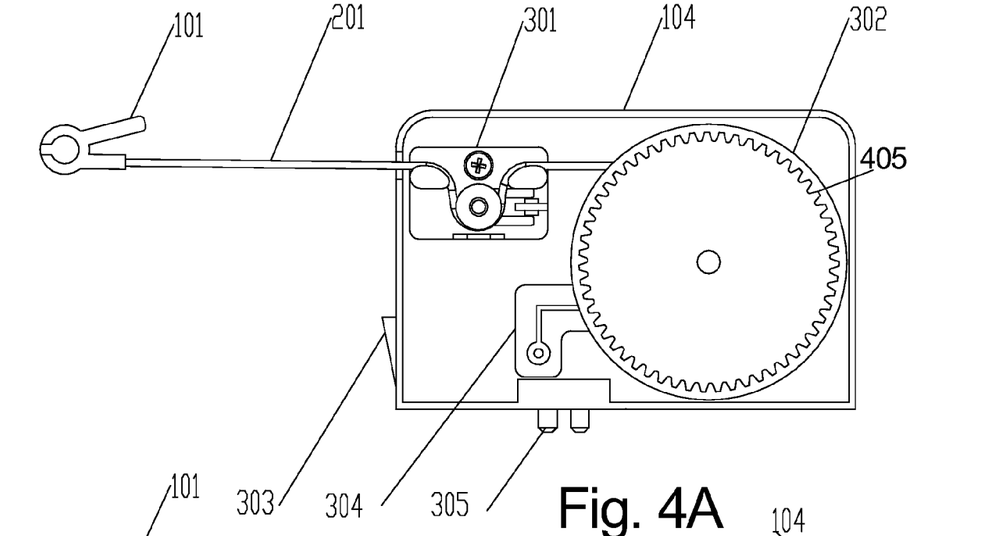
FIG. 4A provides a second sectional view of an exemplary ECG cable management system according to principles of the invention.
Figure 4B:
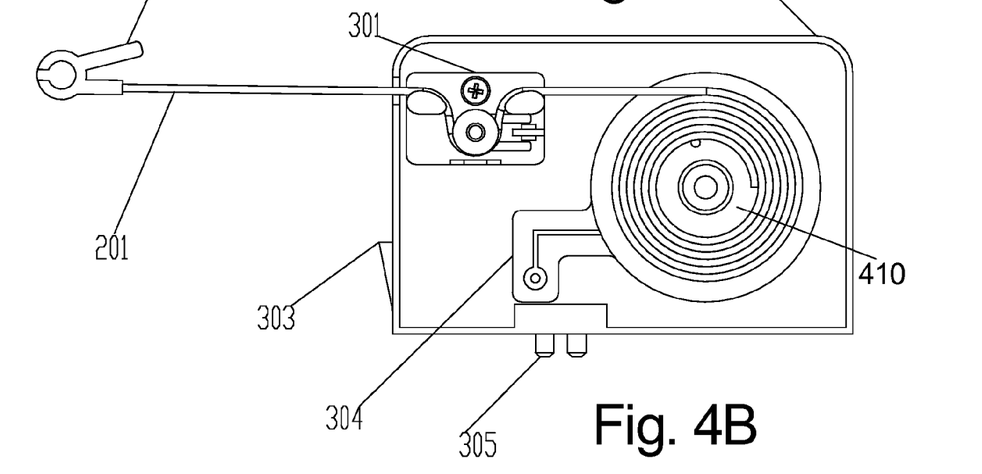
FIG. 4B provides a third sectional view of an exemplary ECG cable management system according to principles of the invention.

Now referring to FIG. 2, the ECG cable management system 2 is shown apart from a table 1 or other support mechanism. A plurality (e.g., six) ECG lead clips 101 extend from the top of the system 2. The lead clips 101 are attached to leads 201 (as shown in FIGS. 4A, 4B), which are also referred to herein as lead wires 201. The lead clips 101 and attached leads 201 may be individually extended from the unit. The exemplary lead clips 101 are configured for releasable attachment to conventional terminals of ECG electrodes attached to a patient. Each lead 201 may be extended to the limit of the lead wire, which, by way of example and not limitation, may be approximately 60 inches.

Also shown are six test terminals 102. The lead clips 101 may be selectively connected to the test terminals 102 to test the lead. Advantageously, the lead clips 101 facilitate testing, which may be carried out periodically or at determined events, such as before each use. In a preferred implementation, when fully retracted, each lead clip 101 should be connected to its respective storage test terminal 102. A test signal may be activated by lead retraction mode and deactivated by lead extension mode.

An electronics module 103 is conceptually shown. As discussed in greater detail below, the electronics module 103 is operably coupled to other components of the system 2, such as to the lead wires 201, test terminals 102, and motors 208, as well as to the power cable 108 and ECG signal cables 109, which communicate ECG signals to one or more monitoring devices. The electronics module 103 comprises circuitry and electronics to enable described functions.

A plurality (e.g., six) lead cartridges 104 are also shown. In the exemplary embodiment, lead wires 201 are supplied in interchangeable cartridges 104 that facilitate replacement of a damaged lead 201, changing the color of a lead, or changing the length or other physical characteristics of the lead wires 201.

The exemplary system 2 is comprised of a plurality of cartridge drive modules 105. One cartridge drive module 105 is provided for each lead wire 201 employed with the system 2. Each cartridge drive module 105 includes a means for releasably engaging a cartridge 104, such as a compartment. The cartridge drive modules 105 may be stackable to facilitate expansion and contraction, thereby easily accommodating various numbers of lead wires facilitating upgrades in the field. An ejector lever 106 is provided on each drive module 105 to controllably release a cartridge 104 from its corresponding cartridge drive module 105. Control buttons 107 are also provided on each drive module 105 to allow an operator to control extension and retraction of lead wires 201.

A power cable 108 and a plurality of ECG signal cables 109 extend from the system 2. The ECG signal cables 109 carry signal data to one or more ECG signal processing devices. Such devices include any compatible equipment capable of receiving and utilizing output signals from the system. Examples of such devices include, but are not limited to, ECG monitors, heart synchronized pumps, heart synchronized imaging devices and any other compatible equipment.

Figure 3:
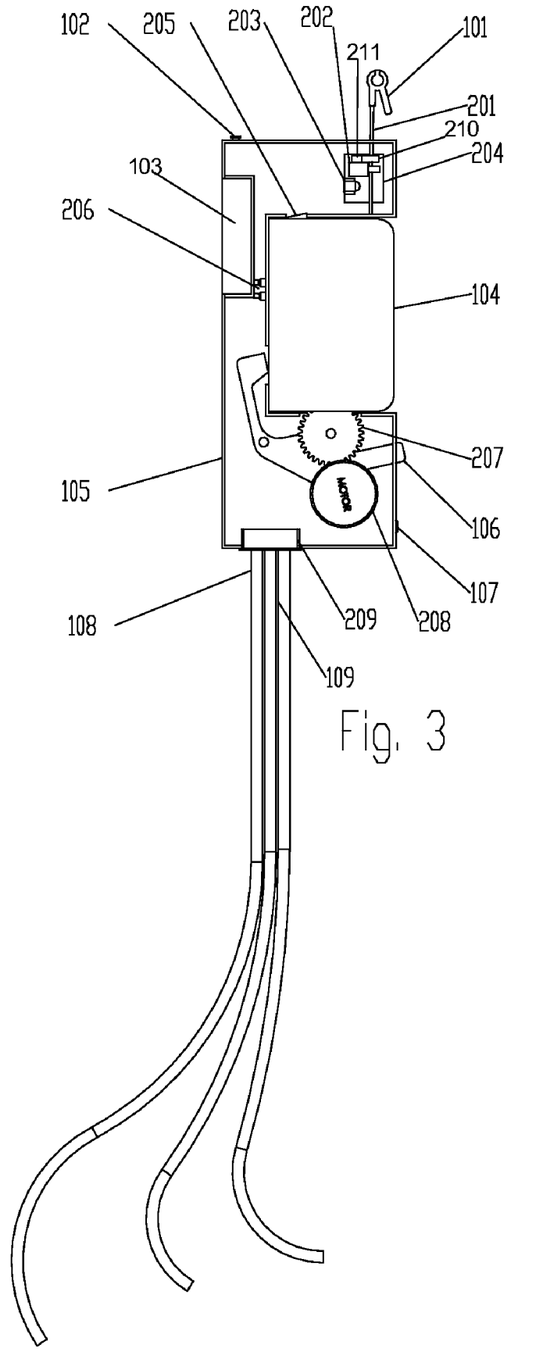
FIG. 3 provides a first sectional view of an exemplary ECG cable management system according to principles of the invention.

Referring now to FIG. 3, a side view of a base cartridge drive module 105 is shown. The base module 105 has the three cables 108, 109 attached as described above. Other modules 105, without the cables 108, 109, may be coupled to the base module to provide a multi-module system 2 with one set of cables 108, 109, such as the system conceptually shown in FIG. 2. The base module 105 (i.e., base cartridge drive module 105) is referred to herein as a primary module. Such other modules 105, without the cables 108, 109, are referred to herein as secondary modules. The exemplary system 2 conceptually depicted in FIG. 2 is comprised of a base module and five secondary modules, though any number of modules may be employed.

Figure 11A:
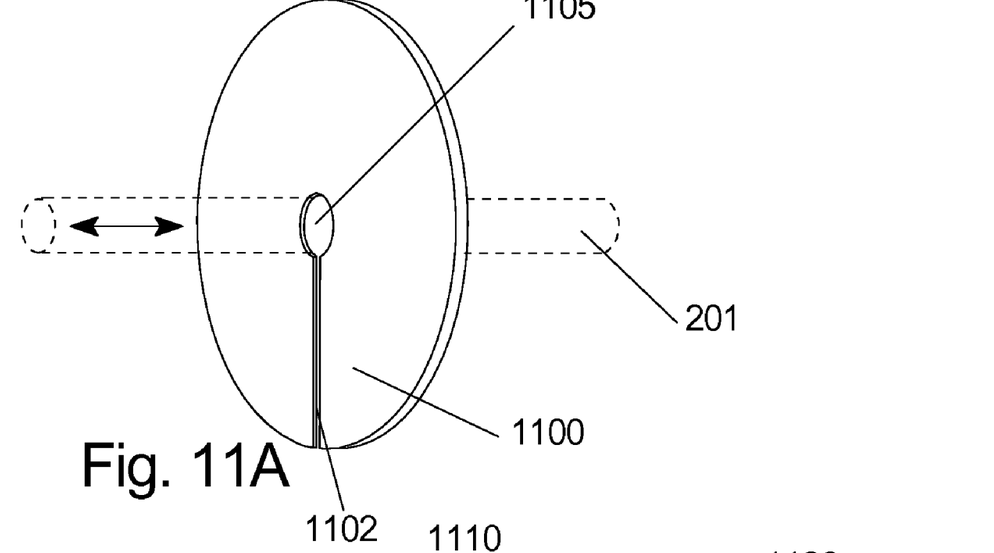
FIGS. 11A and 11B provide perspective views of an exemplary squeegee assembly for an exemplary ECG cable management system according to principles of the invention.
Figure 11B:
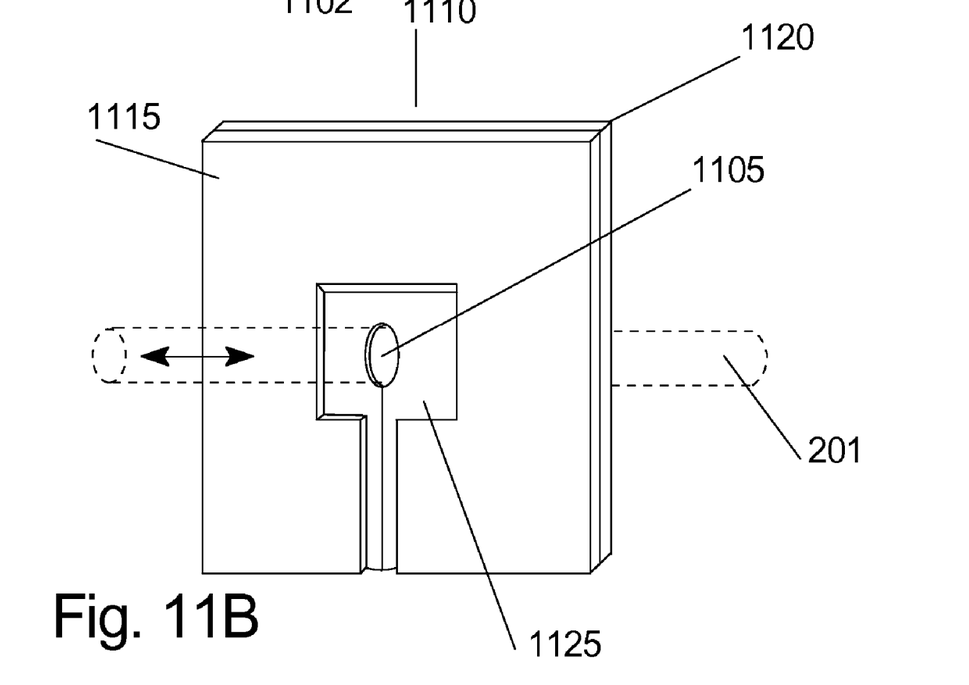

An ECG lead clip 101 is attached to a lead wire 201 which extends into a lead cartridge 104. As the lead wire 201 enters the cartridge drive module 105 it passes through a cleaning assembly 204. In an exemplary implementation, the cleaning assembly 204 comprises a cleaning device such as a squeegee assembly 202, which may be dry or soaked with a cleaning solution. By way of example but not limitation, a suitable squeegee assembly 202 may be comprised of a resilient membrane 1100 (FIG. 11) or washer with an aperture 1105 through which the lead wire 201 passes. A slot 1102 may be provided to facilitate installation of the lead wire 201 into the aperture 1105 of the resilient membrane 1100. The aperture 1105 may have a diameter that is approximately the same or slightly smaller than the diameter of the lead wire 201. The resilient membrane 1100 (FIG. 11) or washer may be secured between front and back halves 1115, 1120 of a squeegee frame 1110 with a frame aperture 1125. The squeegee assembly 202 comprised of the resilient membrane 1100 (FIG. 11) or washer secured within the squeegee frame 1110 may be secured within the cartridge drive module 105. Other forms of squeegees, including squeegees comprised of multiple separate sections may be utilized within the scope of the invention. As the lead wire 201 is retracted, the squeegee assembly 202 sloughs off debris clinging to the wire 210.

Optionally, a disinfectant may be applied to destroy harmful organisms accumulated on the lead wires. In such an embodiment, a disinfectant applicator 210 comprised of a sponge, pad, fabric, other porous material or a brush may be positioned upstream or downstream of the cleaning device 202. The applicator 210 may be impregnated, coated, soaked or saturated with a disinfecting agent. The applicator 210 may be a disposable device that is replaced periodically when it becomes worn or the disinfectant is expended. Optionally, a disinfectant reservoir 211 may be fluidly coupled to the applicator 210 and configured to controllably feed disinfectant to the applicator 210 by gravity and/or capillary action.

In one exemplary embodiment, the cleaning device 202 may be followed by a UV light source 203 to further reduce viable contaminants. Ultraviolet lamps such as UVC featuring a dominant wavelength of about less than 280 nm, also called short wave or "germicidal" lamps, may be utilized. In the exemplary embodiment a UVC LED 203 is shown. Illustratively, low pressure mercury-vapor lamps emit light at wavelengths of about 254 nanometers (nm), which is an effective germicide that may be utilized in a system 2 in accordance with principles of the invention.

A plastic detent 205 may be provided to hold the cartridge 104 firmly in place when installed. A plurality of electrical contacts 206 provide an electrical path from the cartridge 104 to the electronics module 103 as the cartridge 104 is installed. As the cartridge 104 is installed it also presses the ejector lever 106 down causing a drive gear 207 and drive motor 208 to engage a spool gear 405 inside of the cartridge 104.

Also shown in FIG. 3 is a cable adapter assembly 209. The cable adapter assembly 209 is used only in a base cartridge drive module 105. A power cable 108 and a plurality of ECG signal cables 109 are connected to the cable adapter assembly 209. Thus, the cable adapter assembly 209 allows for interconnection of the system with an external power supply and ECG equipment.

A mechanism is provided to retract a lead wire 201 by winding it onto a spool and extend a lead wire 201 by unwinding it from the spool. A system 2 according to principles of the invention may include a manual, motorized or spring driven rotation mechanism to controllably rotate a spool within a cartridge 104 onto which a lead wire 201 is unwound and wound for extension and retraction. In an exemplary embodiment a bi-directional motor 208 and drive train comprising a drive gear 207 controllably power the rewinding of the lead wire 201 onto the spool 302 within the cartridge 104. In the case of a spring-driven rotation mechanism, the spring may be charged as the lead wire 201 is withdrawn and then relaxed as the wire is rewound to the cartridge 104. Optionally, the drive gear 207 and motor 208 may comprise a single drive mechanism configured to retract all leads at the same instance and rate.

Figure 10:
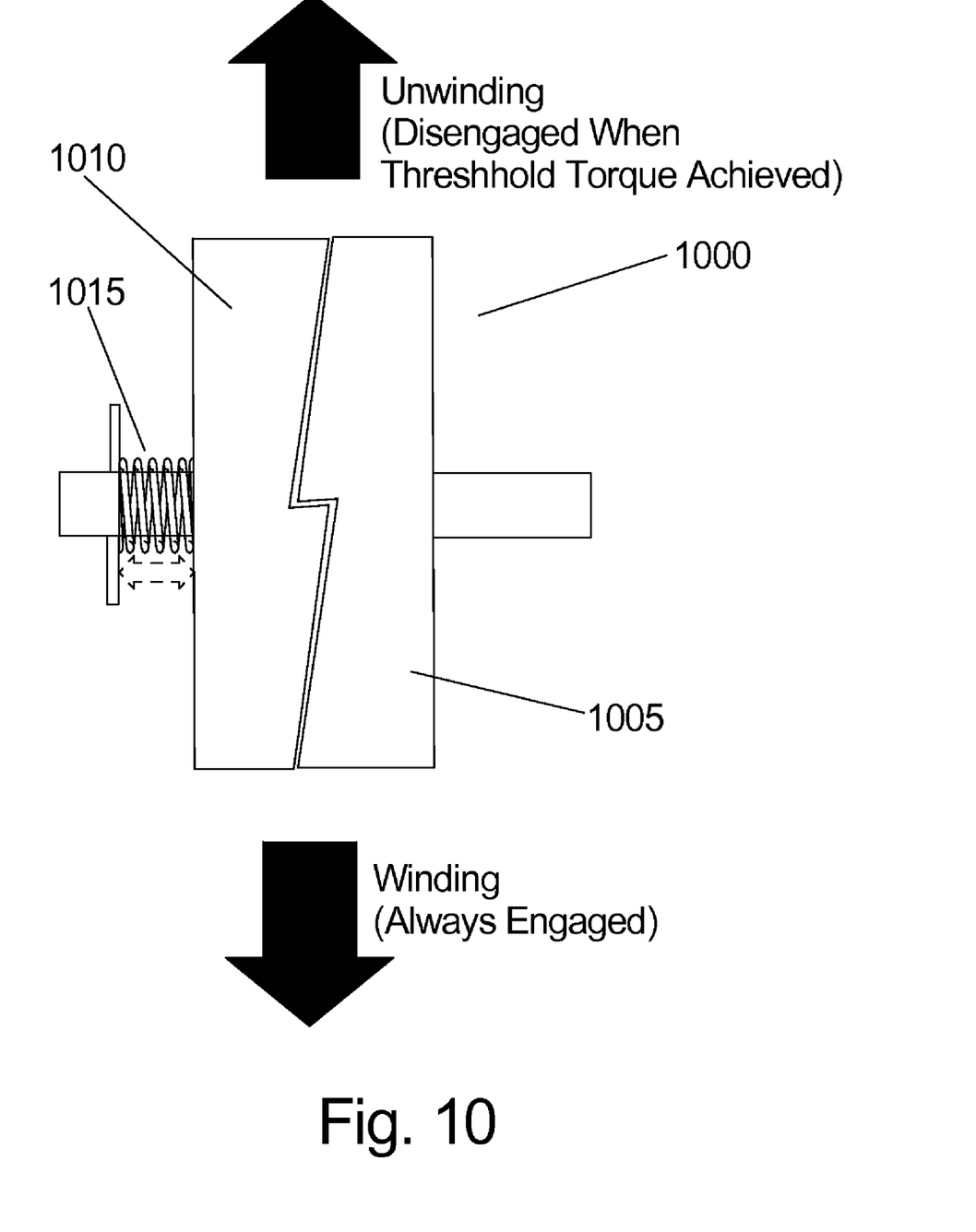
FIG. 10 provides a plan view of an exemplary clutch assembly for an exemplary ECG cable management system according to principles of the invention.

The drive train may optionally include a clutch operably disposed between the drive gear 302 and motor 208, such that the motor 208 will not resist manual extension (i.e., pulling) of the leads towards a patient for application. The clutch may be manually or automatically actuated. By way of example and not limitation, a torque slipping clutch mechanism 1000 (FIG. 10) may engage the drive during unwinding (extension) action until a determined torque is achieved, indicating that the lead wire 201 is being pulled for extension. Upon achieving such a torque, the clutch releases, thereby allowing the spool to freely rotate in an unwinding direction without forcing the motor 208 to rotate in an unwinding direction. Release may be accomplished by exerting a force against a compression spring 1015, and allowing clutch sections 1005, 1010 to separate. Other release mechanisms, such as magnetic and frictional mechanisms, may also be employed to enable release. When the torque subsides or the direction of spool rotation changes (i.e., changes from unwinding to winding), the clutch re-engages, thereby transmitting torque between the spool 302 and motor 208.

Referring now to FIGS. 4A and 4B, cutaway views of a cartridge 104 are provided. FIG. 4A shows the interior of a cartridge 104 with a lead wire spool 302 intact. The spool 302 comprises a spindle 410 (FIG. 4B) or cylinder with flanges, on which lead wire may be wound. One flange includes drive teeth 405 configured for engagement with drive gear 207. A detent barb 303 is provided to snap and secure the cartridge 104 into position. A brush circuit board 304 collects signals from a spool slip ring circuit board (discussed below). The brush circuit board 304 includes one or more (e.g., four) spring contacts 307 (FIG. 5A), each configured to rub against an electrically conductive slip ring 306 (FIG. 5B) on the spool. A plurality of electrical contacts 305 is also provided. The electrical contacts 305 carry information from the lead wire 201 and strain gauge assembly 301 to a corresponding cartridge drive module 105 to be relayed to the electronics module 103.

The lead wire 201 is routed through a cable strain gauge assembly 301 configured to measure tension on the lead wire 201 and provide an analog signal to the electronics module 103. An exemplary strain gauge assembly 301 includes one or more resistive elastic sensors, the resistance of which is a function of applied strain (unit deformation). The electronics module 103 processes the analog signal from strain gauge assembly 301 to monitor and/or control the spool drive motor 208.

Figure 9A:
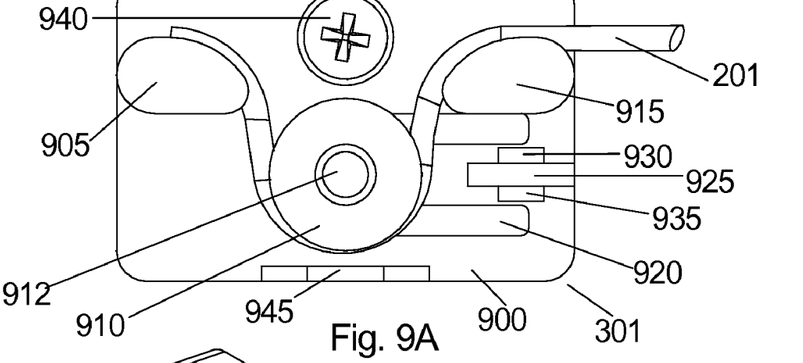
FIGS. 9A, 9B and 9C provide front plan, front perspective, and rear perspective views of a cable strain gauge assembly for an exemplary ECG cable management system according to principles of the invention.
Figure 9B:
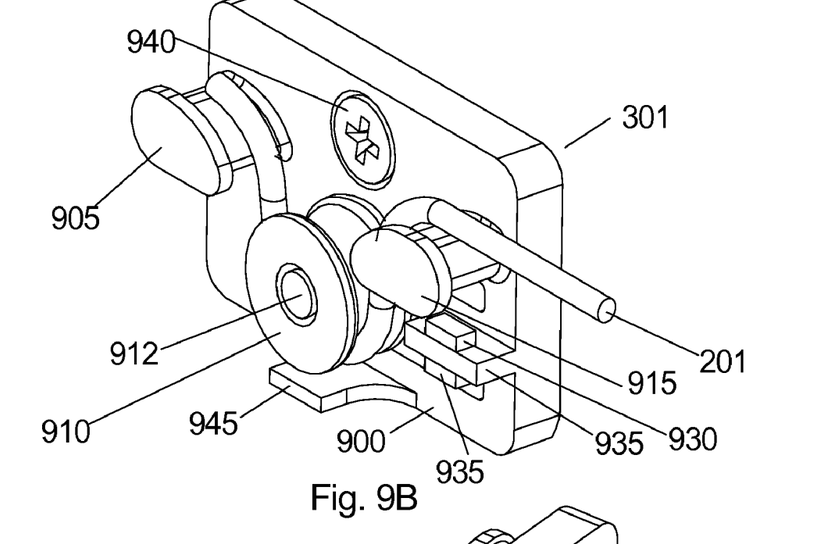
Figure 9C:
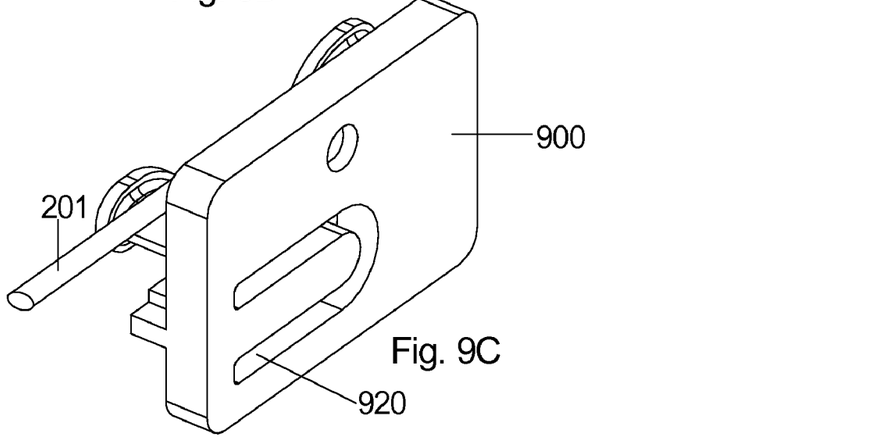

Various strain gauge assemblies may be employed in accordance with the principles of the invention to convert lead wire tension into an electrical signal suitable for processing by the electronics module 103. In an exemplary embodiment, as shown in FIGS. 9A, 9B and 9C, the cable strain gauge assembly 301 includes a base 900 and a fastener 940 for securing the assembly to the cartridge 104. The lead wire 201 travels over a downstream guide 905, around a portion of a flanged roller 910, over an upstream guide 915 and then to the spool 302. The flanged roller 910 and a corresponding roller guard 945 keep the lead wire 201 on track even when tension is released. The roller 910 includes a shaft 912 affixed to a cantilever 920 formed in the base 900. The roller 910 may rotate and with greater tension displace the cantilever 920 upward, causing a signal to be generated in the strain gauge elements near the fixed end of the cantilever 920. The strain gauge elements 930, 935 are mounted to a strain gauge base 925 and provided near the fixed end of the cantilever 920 to sense strain. When the lead wire 210 is tensed, the roller exerts a force against and generates a strain or deflection in the cantilever beam 920. The strain or deflection in the cantilever beam 920 causes the resistive strain gauge elements 930, 935 to produce analog signals.

The strain gauge assembly may be calibrated during manufacture to supply a standardized voltage signal at one or more determined strain levels, for wires having various tensile strengths. By way of example and not limitation, the strain gauge assembly may be adapted to produce signals indicating acceptable tension, maximum acceptable tension and/or unacceptable (i.e., excessive) tension for any given type of wire. In this manner, the system will avoid overstressing whatever type of wire may be used, thereby guarding against structural failure of the wire.

Referring again to FIG. 4B, the interior of a cartridge 104 with a lead wire spool 302 is shown. The flange with drive teeth 405 is removed to reveal lead wire 201 coiled on the spool 302. In the exemplary embodiment, the width of the spool spindle 410 is approximately equal to the diameter of the lead wire 201, allowing only a single column winding. However, greater widths may be utilized to allow multiple column windings.

Figure 5A:
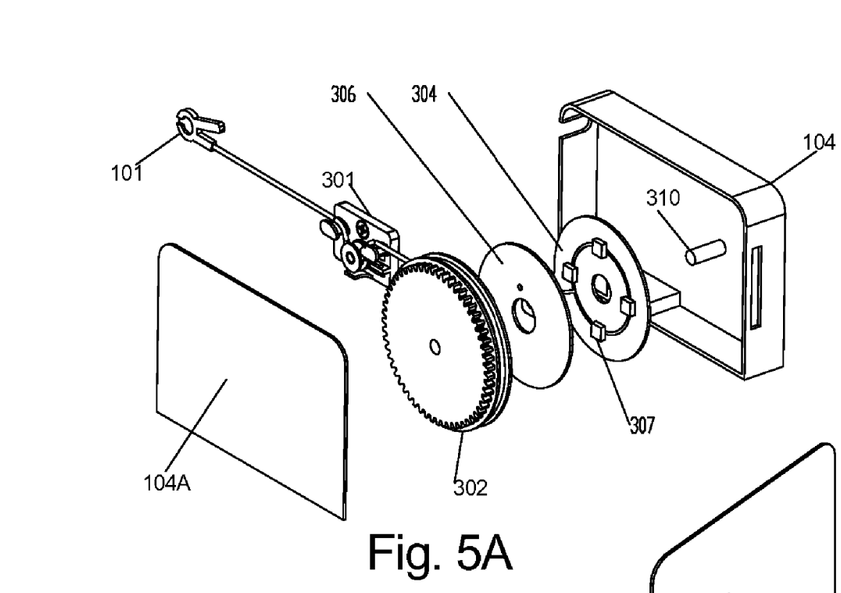
FIG. 5A provides a first exploded view of an embodiment of an exemplary ECG cable management system according to principles of the invention.
Figure 5B:
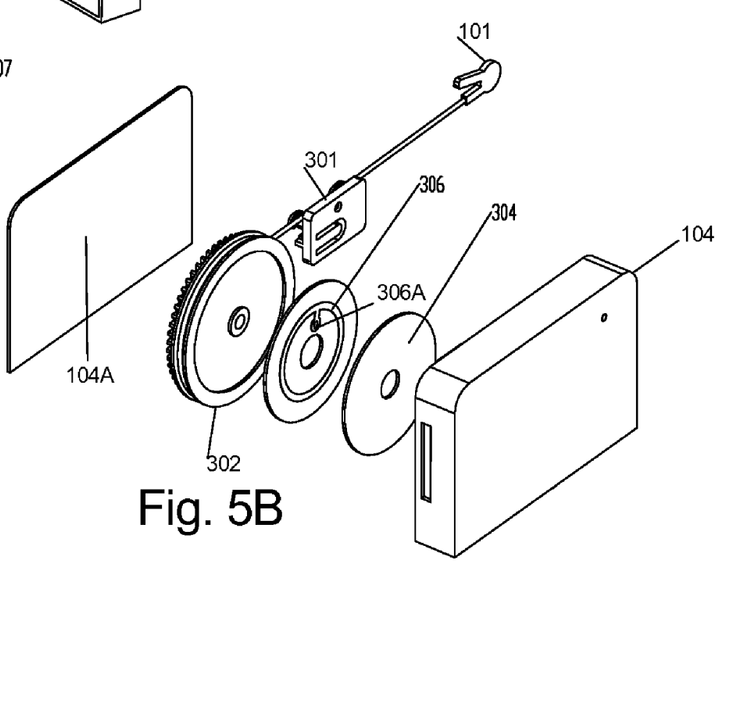
FIG. 5B provides a second exploded view of an embodiment of an exemplary ECG cable management system according to principles of the invention.

FIGS. 5A and 5B provide exploded views of the cartridge 104. A removed cover 104A reveals the internal components. The electrically conductive slip ring 306 may be permanently mounted to the inside flange of the wire spool 302. A connector 306A such as a solder point is provided near the hub. The inside end of the lead wire 201 may be attached to the connector 306A. The slip ring 306 features a circular pattern coaxial to the hub of the spool, forming a continuous electrode. The spring contacts 307 of the brush circuit board 304 electrically engage slip ring 306. The brush circuit board 304 is attached to the wall of the cartridge and is stationary. Together, the slip ring 306 with the connector 306A and the spring contacts 307 of the brush circuit board 304 comprise means for communicating a signal from lead wires 201 on a rotating spool. A spindle 310 is provided for rotationally mounting the wire spool 302. Alternative methods of collecting a signal from a rotating object are known in the art. The method described herein is merely one example. Other methods that are suitable for collecting a signal from a rotating spool of wire may be utilized and are intended to come within the scope of the invention.

Figure 6:
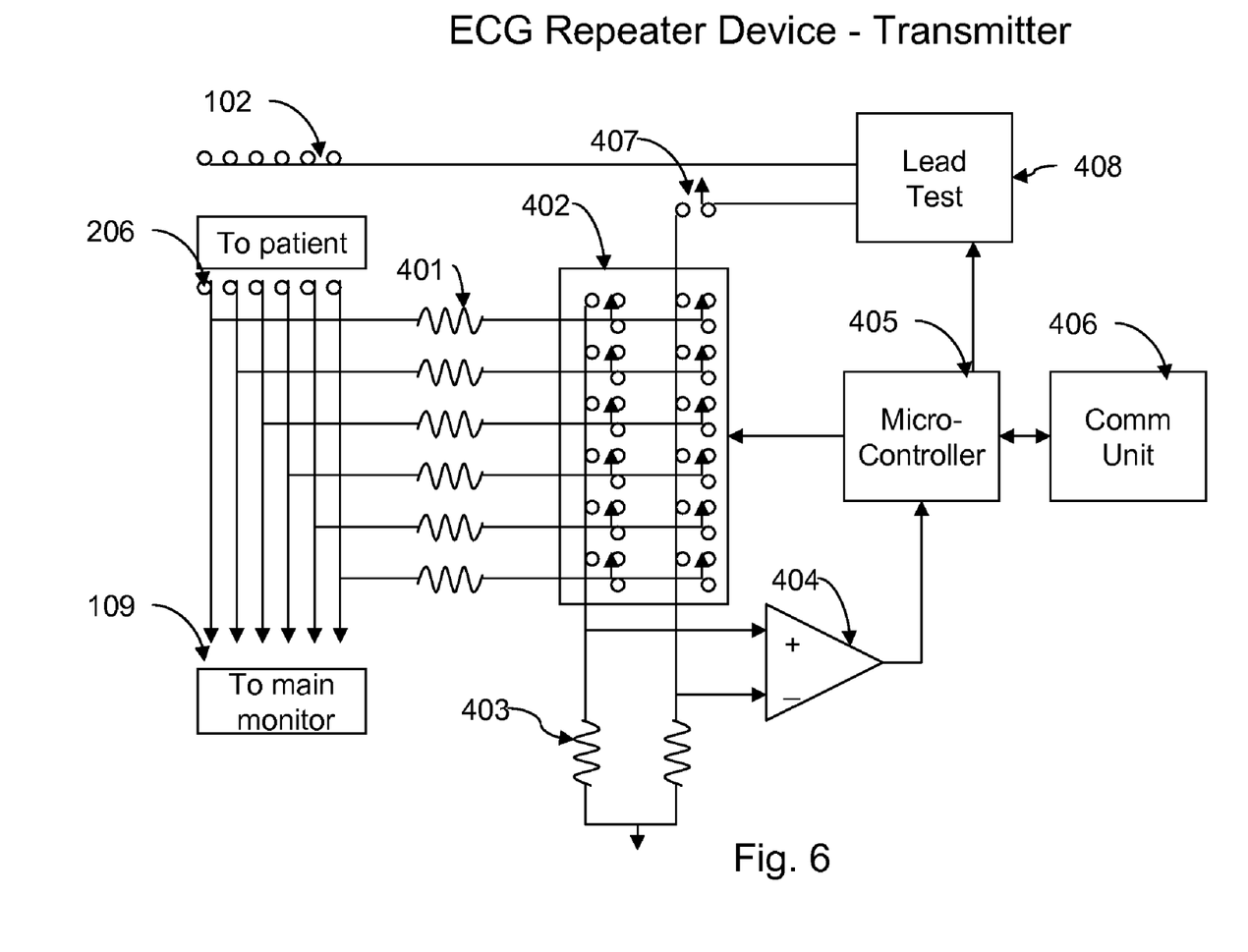
FIG. 6 provides a high level block diagram of circuitry for an exemplary ECG cable management system according to principles of the invention.

An exemplary electronics module 103, as conceptually shown in FIGS. 1, 2, and 3, is comprised of various electronic components, which are described below and depicted in the high-level schematic drawings provided as FIGS. 6, 7 and 8. Referring to FIG. 6, a schematic diagram is provided that conceptually illustrates principal components of an exemplary signal repeater transmitter 600 according to principles of the invention. The individual components and sub-systems may be available from prior art and other devices available in this industry. The selection, configuration, arrangement and coordination of the exemplary components and sub-systems provide unique circuitry that is particularly effective for use with an electronics module 103 for a system 2 according to principles of the invention. Additionally, the described embodiment includes technology to allow unique pair and polarity selection abilities.

The exemplary electronics module 103 comprises electronic technology configured to allow more than one ECG monitoring device to observe/receive signals from a single set of leads to the patient. The exemplary electronics module 103 also enables testing of lead wires 201 and their terminals 101, as mentioned above.

Sensitive circuitry of the electronics module 103 must be protected from defibrillation pulses. In addition, loading of the electronics module 103 by the relatively low impedance of a defibrillator output must be prevented. Moreover, it is desirable to protect an implanted defibrillator from external defibrillator pulses. To address these potential problems, a defibrillator protection sub-system 601 is provided. The defibrillator protection sub-system 601 is configured to protect the electronics module 103 from the discharge of a defibrillator. Optionally, the defibrillator protection sub-system 601 may also include components to help isolate the electronics module 103 and prevent it from interfering with measurements of the main ECG monitor being employed. While the defibrillator protection sub-system 601 is represented in FIG. 6 by a resistor 601 for each lead wire 201, there are many defibrillator protection devices known in the art to provide the desired protection. Such devices come within the scope of the invention.

A crossbar transfer switch 602 is also provided in an exemplary embodiment. The crossbar transfer switch 602 is configured to allow any ECG signals received via lead wires 201 to be applied to either inverting or non-inverting inputs of the instrumentation amplifier 604. The crossbar transfer switch 602 may be an electromechanical switching device or an electronic analog switch that performs as described. The desired connections may be selected by the microcontroller 605 using an internal program or from remote commands.

An alternate sub-system and method for transmitting all signals from all lead wires 201 concurrently is to use the same number of operational amplifiers as lead wires 201 being monitored. In such an embodiment, signals from all lead wires 201 may be measured relative to signals from one lead wire (i.e., reference signals), and the relative signals may be subtracted from the reference signals to recreate the original lead signal.

A reference voltage 603 source is provided to allow measurements of signals relative to some internal or external voltage reference. The reference voltage 603 source may allow measurement of unbalanced signals. The reference voltage 603 source may be derived from any one, or a combination, of the ECG leads or from an internal voltage source.

An instrumentation amplifier 604 is also provided in the exemplary embodiment. The instrumentation amplifier 604 is an analog device configured to produce a low impedance signal output that is proportional to the difference between the signals applied to inverting and non-inverting inputs. In an exemplary implementation, the device must have a very high input impedance, e.g., >20 megohms.

An exemplary electronics module 103 also includes a microcontroller 605. The microcontroller supplies control signals that select which leads are connected to which inputs on the instrumentation amplifier 604. It may also contain an analog to digital converter subsystem adapted to measure analog voltages and represent them as digital data. It may communicate with the communications sub-system 606 to send and receive information with a remote signal receiver device. To enable communications, the microcontroller 605 may run some communications protocol.

The microcontroller 605 may govern in a predetermined manner the performance of the electric motor 208. The microcontroller 605 governs starting and stopping the motor and the direction of rotation in response to user selection of control buttons 107 provided on each drive module 105. Additionally, the microcontroller may regulate or limit torque, and protecting against overloads and faults, based on signals from the strain gauge assembly 301. In the extract mode, as the user applies any tension to a lead, that motor 208 is instructed to unwind that lead wire until there is no tension sensed by the strain gauge assembly 301 and measured by the microcontroller 605. In a similar fashion, when the unit is in the retract mode, the microcontroller 605 means commands the electric motor 208 to retract the lead until the maximum safe tension is reached. If the tension should begin to exceed this level, then the microcontroller 605 will reverse the electric motor 208 and extend the wire to relieve the excess tension.

A communications unit 606 is also provided. The communications unit 606 comprises circuitry configured to carry digital information to and from the electronics module 103. The communications unit 606 may employ wired, radio frequency (RF), and/or optical communication media. The communications unit 606 may be configured to receive and controllably communicate control data input for the electronics module 103, and to receive and controllably communicate signal data output from any one or combination of the lead wires 201.

Test terminals 102 are provided for each lead wire 201. The lead clips 101 may be selectively connected to the test terminals 102 to test the lead. A test signal is produced by the lead test generator 608. The lead test generator 608 and the test signal switch 607 are controlled by the microcontroller 605. During a test phase, one side of the lead test generator 608 is applied to the test terminals 102. The other side of the lead test generator 608 is applied to the non-inverting input of the instrumentation amplifier 604. An AC waveform of known phase and amplitude is applied to the leads and the microcontroller 605 tests the output signal from the instrumentation amplifier 604 to verify it is being carried by the lead without distortion or loss. Each lead may be tested by the instrumentation amplifier 604, one lead at a time, by switching one lead at a time to the inverting input of that amplifier.

Figure 7:
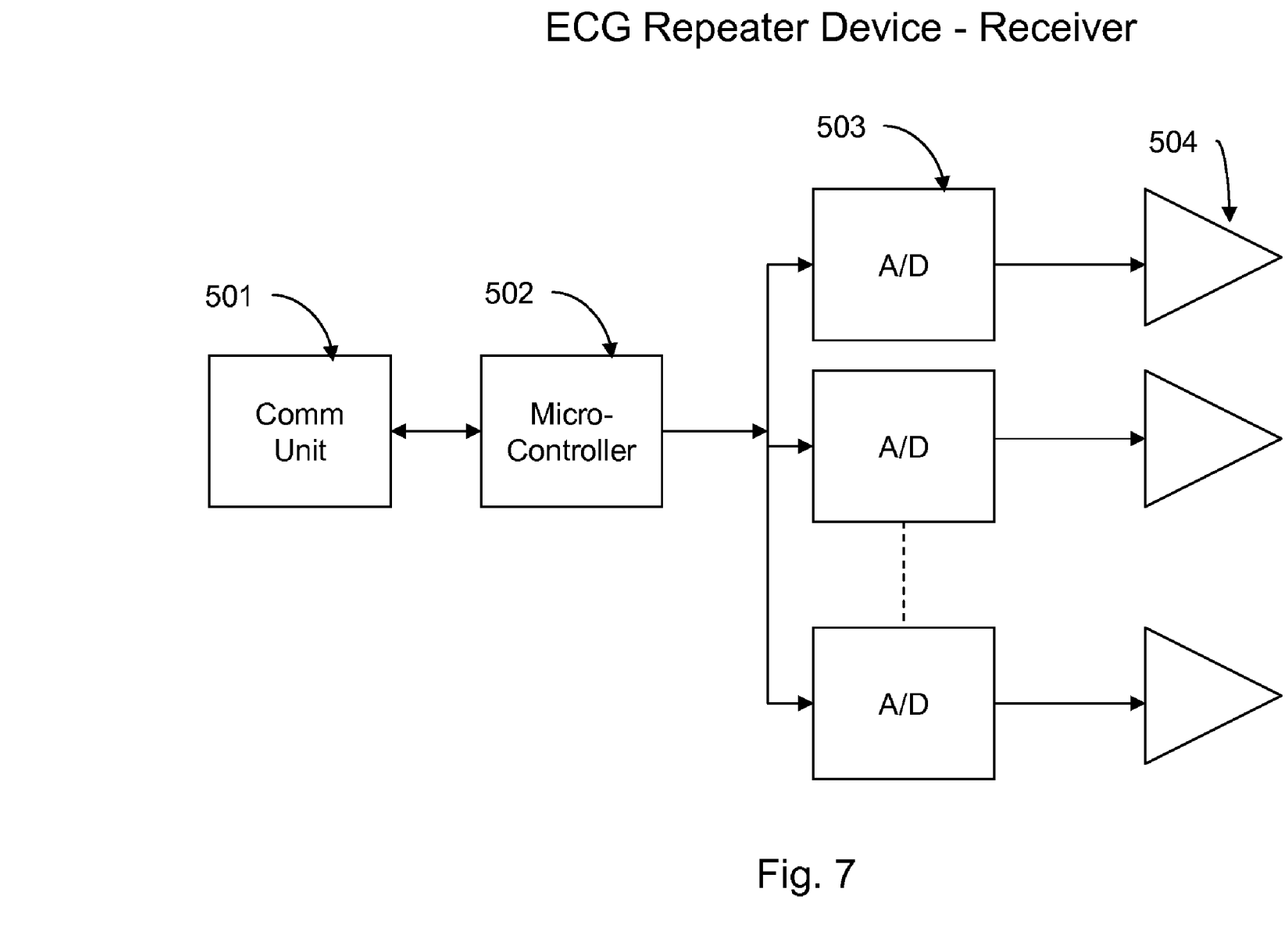
FIG. 7 provides a high level block diagram of receiver circuitry for an exemplary ECG cable management system according to principles of the invention.
Figure 8:
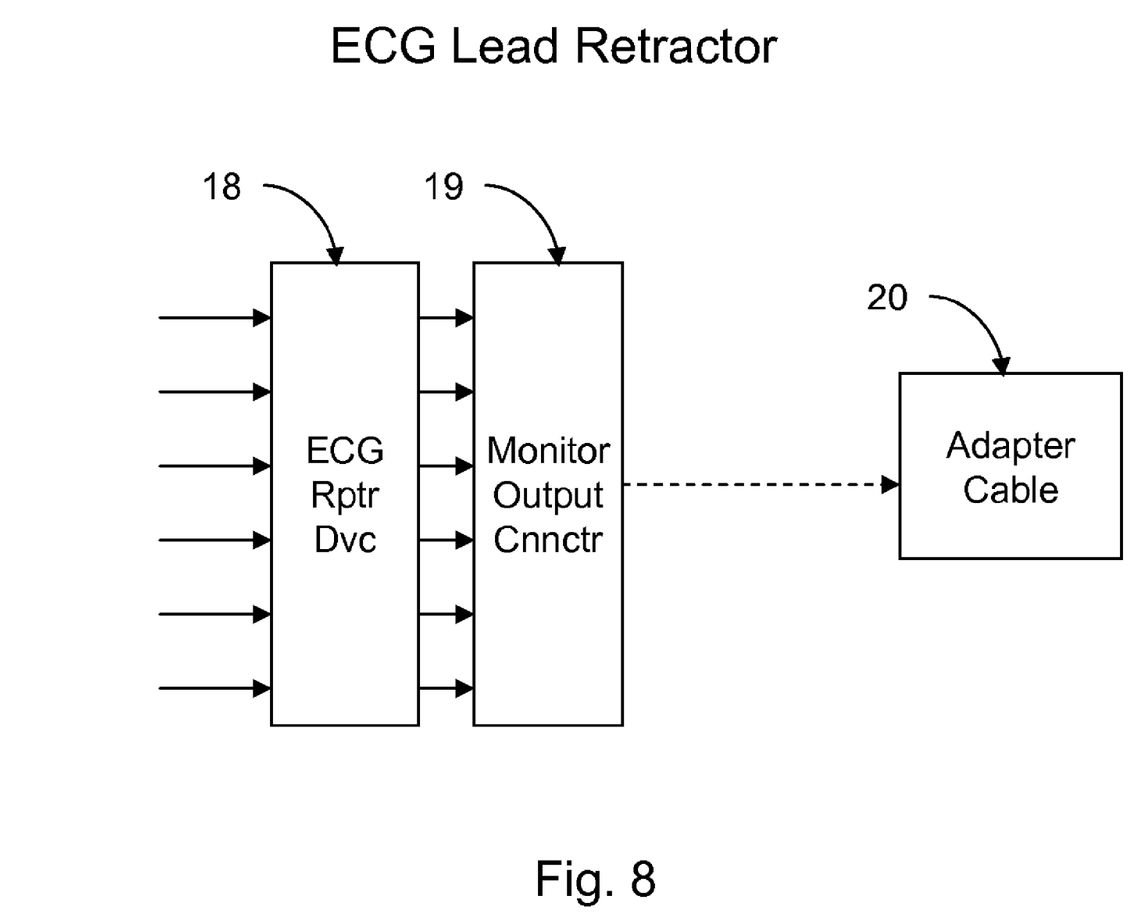
FIG. 8 provides a high level block diagram of circuitry for an exemplary ECG cable management system according to principles of the invention.

Referring now to FIG. 7, the electronics module 103 also includes a receiver unit 700. The receiver unit 700 reproduces the digitally encoded analog signals. An analog communications unit 701 transmits signals from lead wires 201 to a microcontroller 702. The receiver microcontroller 703 communicates the analog signals to analog/digital converters 703. The analog to digital converters 703 convert continuous lead wire 201 signals (i.e., voltages) to discrete digital data (i.e. binary numbers), thereby creating a data set that can be stored in a memory and processed by a microprocessor. In general, the sampling frequency should be at least approximately double that of the maximum frequency component of the observed lead wire 201 signals to avoid aliasing. Signals from the analog/digital converters 703 are fed as input to amplifiers 704, which magnify the input signals to yield significantly larger output signals. The amplifiers 704 may be operational amplifiers which employ external feedback for control of their transfer function and gain.

A monitor output connector 209 is disposed between the plurality of ECG signal cables 109, which communicate ECG signals to one or more monitoring devices, and the electronics module 103. The monitor output connector 209 supplies connections to the ECG signal cables 109 and a grounded signal shield. This connector 209 attaches the appropriate ECG signal cables 109 for the model of ECG monitor being used. The ECG signal cables 109 comprise a mating connector for the cable adapter assembly 209 at one end and the specific ECG input connector required by the ECG monitor being used, at the opposite end. Various ECG signal cables 109 may be available to accommodate the variety of monitors and ECG devices used in the industry.

Optionally, a universal adapter cable may be provided as the ECG signal cable 109. The universal adapter cable terminates in simple terminal posts rather than a specific monitor interface, so that standard lead clips may be used to make the connections.

Those skilled in the art will appreciate that the exemplary ECG cable management system 2 according to principles of the invention addresses several issues related to reuse of ECG leads, and multiple devices in a clinical environment that may require access to the signals from a patient's heart. To address these issues the invention provides an automated lead wire storage system 2 that facilitates efficient lead storage and reuse, while avoiding the common tangling of leads between uses. The invention also provides devices to clean and disinfect the lead wires between uses, to prevent accidental over-tensioning of lead wires that could damage them and their signal quality, to test lead wires before use, and to control the selection and polarity of signals being sent to monitoring devices.

The ECG cable management system 2 is interposed between heart monitoring equipment and ECG leads attached to the patient. The system 2 employs interchangeable cartridges 104 that allow selection of various wire types and colors to support the preferences of the operator and requirements of the procedure. The system 2 is scalable to any number of signal leads attached to a patient. The embodiment described above uses six leads, but the principles of the invention apply to more or fewer leads. The system 2 employs adapter cables 109 to match the input cables of various ECG monitoring devices. The electronics module 103 allows a single set of leads attached to the patient to feed necessary signals to a plurality of devices that may require these signals. The ECG cable management system 2 may be fitted with any number of adapter cables to match various devices input connectors. In some embodiments these various devices may require signal isolation by optical isolators or other similar means.

During use, an operator may employ the test terminals 102 to assess the condition of the leads. An indicator (e.g., an LED) may be provided to show the operability of each lead. Next, the operator may set the ECG cable management system 2 for lead extension. Buttons 107 on determined cartridge drive modules 105 may be selectively actuated for extension (unwinding) of their lead wires, while others may remain tightly stored. Additionally, an "extract all" button or control may be provided to put all leads in the extract mode. Illustratively, rapidly pressing the unwind button 107 on the primary module twice or three times within a determined time period (e.g., five seconds) may cause extension of all lead wires.

While in the extract mode, when a lead clip 101 is disconnected from its storage test terminal 102, there is a strain gauge assembly 301 in the lead cartridge 104 monitoring the tension on that lead. As the operator begins to pull on that lead to place it on the patient, this sensor sends a signal to the microcontroller 605 which in turn activates the drive motor 208 causing it to feed out wire at a rate that keeps the wire tension below a specified level. When the tension on the lead is below this tension level, the drive motor 208 is de-energized. In this fashion, an operator may easily withdraw as much lead length as is needed to reach a particular body terminal on the patient that is intended for that lead. After it is connected, there is no tension on the lead. This procedure is repeated for the plurality of leads specified for the given operation.

Prior to use, the ECG cable management system 2 may be connected to one or more monitoring devices needed for a scheduled procedure. Upon completion of a procedure, the lead clips 101 may be disconnected from the patient one at a time and after each one is disconnected, that cartridge drive module 105 may be switched to retract mode. In retract mode, the microcontroller 605 activates the drive motor 208 causing the spool 302 to wind and draw the wire into its cartridge 104. The rewinding process is once again controlled by signals from the strain gauge assembly 301 in the lead cartridge 104 monitoring the tension on that lead. During retraction, as the tension on the lead rises to a specified limit, the microcontroller 605 slows the drive motor 208 so as to keep the tension on the lead at a safe level to prevent damage to the lead. Optionally, during retraction there may be a preprogrammed maximum speed of retraction to ensure that the lead wires traverse the cleaning assembly 204 slowly enough to guarantee that cleaning is optimal.

When fully retracted, each lead clip 101 may be reconnected to its respective storage test terminal 102. The test signal may be activated by lead retraction mode and deactivated by lead extension mode, as determined by the microcontroller 605.

The electronics module 103 contains a microcontroller 605 to monitor controls and sensors as described above. It also provides speed and direction commands to the drive motor 208 means. It may also incorporate analog to digital converters to facilitate digital transmission of ECG information. Additionally, the microcontroller 605 may manage communications through any sort of communications medium to send data and receive control information. Furthermore, the microcontroller 605 controls the crossbar transfer switch 602. By selectively closing a pair of switches it can cause any pair of leads to be connected to the instrumentation amplifier 604, inverting or non-inverting inputs. This flexibility of connection allows better use of the signals available to the signal repeater components and provides an alternative to the known method of referencing all leads to one common patient lead. The crossbar system described above may also reference all leads to one common patient lead, as known in the prior art.

A power supply such as one or more batteries and/or an AC adapter may be provided to supply electrical energy to the system 2. Disposable batteries or rechargeable batteries may be utilized. Optionally, an AC adapter may be provided to convert AC power supplied by a utility company to a well-regulated lower voltage DC power suitable for the system 2.

A controllable extension and retraction mechanism in accordance with the principles of the invention may be used for other flexible products that require safe extension and then retraction by mechanical means, e.g.—an electric steam iron power cord. The use of tension gauges and intelligent control of drive motors in accordance with the principles of the invention could be applied to these applications.

While an exemplary embodiment of the invention has been described, it should be apparent that modifications and variations thereto are possible, all of which fall within the true spirit and scope of the invention. With respect to the above description then, it is to be realized that the optimum relationships for the components of the invention and steps of the process, including variations in form, function and manner of operation, are deemed readily apparent and obvious to one skilled in the art, and all equivalent relationships to those illustrated in the drawings and described in the specification are intended to be encompassed by the present invention. The above description and drawings are illustrative of modifications that can be made without departing from the present invention, the scope of which is to be limited only by the following claims. Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents are intended to fall within the scope of the invention as claimed.

What is claimed is:

1. A cable management system comprising an electronics module; a plurality of drive modules and a cable cartridge for each drive module;

each cable cartridge including a housing defining an interior compartment and a cable opening configured to allow a cable to pass from the interior compartment through said cable opening; said cable cartridge further including a cable spool rotatably mounted in the interior compartment of the housing and having an electrical slip ring; an electrically conductive lead wire having a first end and an opposite second end, said first end being mechanically attached to said spool and electrically connected to said slip ring, said lead wire being adapted for transmitting electrical signals; and a stationary electrical contact in electrical communication with said slip ring; and each drive module including means for electrically coupling said stationary electrical contact to said electronics module; means for releasably engaging a cable cartridge; means for controllably rotating said cable spool; and means for communicating output signals from said electronics module to output signal cables.

2. A cable management system according to claim 1, wherein each drive module further includes an ejector configured to controllably release the corresponding cable cartridge from the drive module.

3. A cable management system according to claim 1, wherein each drive module further includes at least one control device operably configured to control extension and retraction of the lead wire for the corresponding cable cartridge.

4. A cable management system according to claim 1, wherein the output signal cables are adapted to communicate output signals to at least one ECG signal processing device.

5. A cable management system according to claim 1, wherein said means for controllably rotating said cable spool comprises a controllable drive motor and transmission adapted to transmit torque from said controllable drive motor to said cable spool.

6. A cable management system according to claim 1, wherein said means for controllably rotating said cable spool comprises a controllable drive motor communicatively coupled to said electronics module, said electronics module being configured to govern rotation and direction of said drive motor, and further comprises a transmission adapted to transmit torque from said controllable drive motor to said cable spool.

7. A cable management system according to claim 1, wherein said means for controllably rotating said cable spool comprises a controllable drive motor and transmission adapted to transmit torque from said controllable drive motor to said cable spool, said transmission including a torque slipping clutch mechanism adapted to transmit torque except when a determined torque is exceeded.

8. A cable management system according to claim 1, wherein said means for controllably rotating said cable spool comprises a spring-driven rotation mechanism adapted to be charged as the lead wire is extended from the cable opening and adapted to relax as the lead wire is retracted through the cable opening.

9. A cable management system according to claim 1, wherein said electronics module comprises a defibrillator protection sub-system configured to protect said electronics module discharges of a defibrillator.

10. A cable management system according to claim 1, wherein said electronics module comprises a crossbar transfer switch and an instrumentation amplifier having inverting and non-inverting inputs, said crossbar switch being configured to selectively apply input signals received via the lead wire to one of inverting and non-inverting inputs of the instrumentation amplifier.

11. A cable management system according to claim 1, wherein said electronics module comprises a communications unit configured to communicate signals to and from said electronics module.

12. A cable management system according to claim 1, wherein each drive module further comprises a test terminal corresponding to each lead wire;

each lead wire including a lead clip attached at the second end of the lead wire, and said test terminal being adapted for engagement by the lead clip, and said test terminal being operably coupled to said electronics module;

said electronics module including a microcontroller configured to produce a test signal for the test terminal, said test signal being adapted to test integrity of the lead wire.

13. A cable management system according to claim 1, further comprising wherein said means for communicating output signals from said electronics module to output signal cables comprises a monitor output connector disposed between said output signal cables and the electronics module.

14. A cable management system according to claim 1, wherein said cable cartridge further comprises a cleaning assembly adjacent to the cable opening and adapted to clean portions of the lead wire passing through the cable opening.

15. A cable management system according to claim 14, wherein said cleaning assembly includes a squeegee assembly configured to slough off debris clinging to portions of the lead wire passing through the cable opening.

16. A cable management system according to claim 14, wherein said cleaning assembly includes a disinfectant applicator configured to apply a disinfecting agent to portions of the lead wire passing through the cable opening.

17. A cable management system according to claim 14, wherein said cleaning assembly includes a germicidal UV light source adapted to shine UVC light on portions of the lead wire passing through the cable opening.

18. A cable management system according to claim 1, wherein said cable cartridge further comprises a cable strain gauge assembly configured to produce a strain signal representative of tension on the lead wire.

19. A cable management system according to claim 18, wherein said strain gauge assembly includes at least one resistive elastic sensor, the resistance of which is a function of applied strain.

20. A cable management system according to claim 18, wherein said strain gauge assembly is operably coupled to said electronics module.

* * * * *